(12) United States Patent
Troup

(10) Patent No.: US 9,205,108 B2
(45) Date of Patent: Dec. 8, 2015

(54) TREATMENT OF TRAUMATIC BRAIN INJURY BY USING GALLIUM COMPOUNDS TO REDUCE OXIDATIVE STRESS LEVELS

(71) Applicant: Jan M. Troup, The Woodlands, TX (US)

(72) Inventor: Jan M. Troup, The Woodlands, TX (US)

( * ) Notice: Subject to any disclaimer, the term of this patent is extended or adjusted under 35 U.S.C. 154(b) by 0 days.

(21) Appl. No.: 14/793,531

(22) Filed: Jul. 7, 2015

(65) Prior Publication Data

US 2015/0306138 A1 Oct. 29, 2015

Related U.S. Application Data

(63) Continuation-in-part of application No. 13/584,407, filed on Aug. 13, 2012, now abandoned.

(51) Int. Cl.
| | | |
|---|---|---|
| A61K 33/36 | (2006.01) | |
| A61K 33/24 | (2006.01) | |
| A61K 31/28 | (2006.01) | |
| A61K 9/00 | (2006.01) | |

(52) U.S. Cl.
CPC ............... *A61K 33/24* (2013.01); *A61K 9/0014* (2013.01); *A61K 9/0019* (2013.01); *A61K 9/0043* (2013.01); *A61K 31/28* (2013.01)

(58) Field of Classification Search
CPC ........................... A61K 33/36; A61K 2300/00
See application file for complete search history.

(56) References Cited

U.S. PATENT DOCUMENTS

| | | | |
|---|---|---|---|
| 4,704,277 | A | 11/1987 | Bockman et al. |
| 5,175,006 | A | 12/1992 | Matkovic et al. |
| 5,196,412 | A | 3/1993 | Bradley et al. |
| 5,700,487 | A | 12/1997 | Gerber et al. |
| 6,203,822 | B1 | 3/2001 | Schlesinger et al. |
| 7,119,217 | B2 | 10/2006 | Jiang et al. |
| 7,354,952 | B2 | 4/2008 | Julian |
| 8,168,214 | B2 | 5/2012 | Bernstein |
| 2008/0113004 | A1 | 5/2008 | Bernstein |
| 2011/0086914 | A1 | 4/2011 | Bailes |
| 2011/0104246 | A1 | 5/2011 | Rogosnitzky |

OTHER PUBLICATIONS

Giza, C.C. and Hovda, D.A., The Neurometabolic Cascade of Concussion, J. Athletic Training. 2001, 36(3), 228-235.
Bailes, J. E. and Mills, J.D., Docosahexaenoic acid reduces traumatic brain injury in a rodent head injury model. J. Neurotrauma. Sep. 27, 2010, 1617-1624.
Mills, J.D.; Bailes, J.E.; Sedney, C.L.; Hutchins, H. and Sears, B., Omega-3 fatty acid supplementation and reduction of traumatic axonal injury in a rodent head injury model. J. Neurosurg. Jan. 2011, 114(1), 77-84.
NIH—National Institute of Neurological Disorders and Stroke (NINDS), Discussion on Traumatic Brain Injury: Hope through Research, Apr. 15, 2011; www.ninds.nih.gov/disorders/tbi/detail_tbi_htm; 19 pages.

Samii, A.; Badie, H.; Fu, K.; Luther, R.R. and Hovda, D.A., Effects of an N-type calcium channel antagonist (SNX 111; Ziconotide) on calcium-45 accumulation following fluid percussion injury. J. Neurotrauma. Oct. 1999, 16(10), 879-92 (Abstract only).
Lee, L.L.; Galo, E.; Lyeth, B.G.; Muizelaar, J.P. and Berman, R.F., Neuroprotection in the rat lateral fluid percussion model of traumatic brain injury by SNX-185, an N-type voltage-gated calcium channel blocker. Exp. Neurol. Nov. 2004, 190(1), 70-8 (Abstract only).
Shahlaie, K.; Lyeth, B.G.; Gurkoff, G.G.; Muizelaar, J.P. and Berman, R.F., Neuroprotective Effects of Selective N-Type VGCC Blockade on Stretch-Injury-Induced Calcium Dynamics in Cortical Neurons. J. Neurotrauma. Jan. 2010, 27(1), 175-187.
McGuire, D.; Bowersox, S.; Fellmann, J.D. and Luther, R.R., Sympatholysis After Neuron-Specific, N-Type, Voltage-Sensitive Calcium Channel Blockade: First Demonstration of N-Channel Function in Humans. J. Cardiovascular Pharmacology. Sep. 1997, 30(3), 400-403.
Humble, S.R., Calcitonin for acute neuropathic pain associated with spinal cord injury. Anaesth. Intensive Care. Jul. 2011, 39(4), 682-86.
Ito, A.; Takeda, M.; Yoshimura, T.; Komatsu, T.; Ohno, T.; Kuriyama, H.; Matsuda, A. and Yoshimura, M., Anti-hyperalgesic effects of calcitonin on neuropathic pain interacting with its peripheral receptors. Mol. Pain. Jun. 7, 2012; 8(1):42 [Epub ahead of print].
Warrell, R.P.; Brockman, R.S.; Coonley, C.J.; Isaacs, M. and Staszewski, H., Gallium nitrate inhibits calcium resorption from bone and is effective treatment for cancer-related hypercalcemia. J. Clinical Investigation. 1984, 73, 1487-1490.
Todd, P. A. and Fitton, A., Gallium nitrate. A review of its pharmacological properties and therapeutic potential in cancer related hypercalcemia. Drugs. Aug. 1991, 42(2), 261-73 (Abstract only).
Genta, Inc. Ganite® (gallium nitrate injection): Important Therapy for a Serious Cancer Complication. , http://www.genta_com/Products_and_Pipeline/Ganite/Ganite.html, 1 page, last accessed Aug. 18, 2011.
Genta, Inc. "Ganite® (gallium nitrate injection)" product efficacy studies from www.ganite.com/hcp/efficacy_studies.shtml, 3 pages, last accessed Aug. 18, 2011.
Genta, Inc. "Ganite TM (gallium nitrate injection)" product literature from www.ganite.com/docs/30105901.BMR8.pdf, 2 pages, last accessed Aug. 18, 2011.

(Continued)

*Primary Examiner* — Gina Justice
(74) *Attorney, Agent, or Firm* — Andrew W. Chu; Craft Chu PLLC

(57) ABSTRACT

The method for treating traumatic brain injury in an individual includes the step of administering a therapeutically effective amount of a pharmaceutically acceptable gallium compound to a blood brain barrier of the individual within a therapeutically effective time period subsequent to the injury so as to reduce secondary injury in a brain of the individual. Secondary injuries include swelling of the brain after the initial injury, secondary lesions, hematomas, and edema. The effective amount and effective time period for the step of administering are established by test results disclosed in the present invention. Gallium compounds are shown to reduce oxidative stress levels in the brain, a metric for treatment of traumatic brain injury or concussion.

18 Claims, 1 Drawing Sheet

(56) References Cited

OTHER PUBLICATIONS 3M, 3M Passive Transdermal Technology webpage excerpt—http://solutions.3m.com/wps/portal/3M/en_WW/3M-DDSD/Drug-Delivery-Systems/transdemal/drug-in-adhesive/, 1 page, last accessed Aug. 5, 2012.

3M, 3M Microneedle Technology webpage excerpt—http://solutions.3m.com/wps/portal/3M/en_VVW/3M-DDSD/Drug-Delivery-Systems/transdermal/microneedle/, 1 page, last accessed Aug. 5, 2012.

Kaur, A. and Kaur, G., Mucoadhesive buccal patches based on interpolymer complexes of chitosan—pectin for delivery of carvedilol. Saudi Pharmaceutical Journal. 2012, 20, 21-27.

Nafee, N. A.; Boraie, N. A. and Ismail, F.A. Design and characterization of mucoadhesive buccal patches containing cetylpyridinium chloride. Acta Pharm. 2003, 53, 199-212.

Labtec GmBH—A tesa Company, Drug delivery to the buccal mucosa or the gingiva, webpage excerpt from http://www.tesa-labtec.com/eng/transfilm/buccal/drug-deliveiy-to-the-buccal-mucosa-or-the-gingiva,3701591.html, first accessed May 5, 2012, 2 pages.

TREATMENT OF TRAUMATIC BRAIN INJURY BY USING GALLIUM COMPOUNDS TO REDUCE OXIDATIVE STRESS LEVELS

RELATED U.S. APPLICATIONS

The present application claims continuation-in-part priority under 35 U.S.C. §120 from U.S. Ser. No. 13/584,407, filed on 13 Aug. 2012, and entitled "TREATMENT FOR CONCUSSION USING GALLIUM COMPOUNDS".

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to treatment of traumatic brain injury in mammals. More particularly, the present invention relates to treatment of concussions as mild to moderate to severe traumatic brain injuries. The present invention also relates to treatments using gallium compounds to reduce oxidative stress levels in the brain, after the injury.

2. Description of Related Art Including Information Disclosed Under 37 CFR 1.97 and 37 CFR 1.98.

Traumatic brain injury or concussion is the leading cause of death in people under the age of 45 in the United States. Data from The Center for Disease Control (CDC) indicate that approximately every 22 seconds someone in the United States sustains a serious traumatic brain injury. Traumatic brain injuries can range from mild to moderate to severe. Traumatic brain injury (TBI) and concussion are used interchangeably. There are about 3.8 million sports and recreational related concussions in the United States every year with 1,365,000 emergency room visits and 52,000 deaths.

The current treatment for traumatic brain injury or concussion is docosahexaenoic acid (DHA). Concussion treatment usually consists of only patient rest for days to months to allow for the brain to heal. Docosahexaenoic acid (DHA) has been found to both successfully treat the brain damage of patients after concussion but also to offer protection and prevent neuron damage if taken prior to a concussion in rat studies. See, for example, Bailes, J. E. and Mills, J. D. Docosahexaenoic acid reduces traumatic brain injury in a rodent head injury model. I Neurotrauma. 2010, Sep. 27, 1617-1624; Mills, J. D.; Bailes, J. E.; Sedney, C. L.; Hutchins, H. and Sears, B. Omega-3 fatty acid supplementation and reduction of traumatic axonal injury in a rodent head injury model. I Neurosurg. 2011, January, 114(1), 77-84 and Bailes, U.S. Pat. App. Pub. No. US2011/0086914, Apr. 14, 2011.

The trauma of cerebral concussion generates compressive, tensile, and rotational forces resulting in diffuse axonal injury. Immediately following the injury there is a sudden intracellular efflux of potassium and an influx of calcium ions producing a hypercalcemia condition in the brain. The concussed brain goes into a period of depressed metabolism with continued increases in calcium potentially impairing mitochondrial oxidative metabolism. The calcium accumulation can lead to cell death and disrupt neurofilaments and microtubules. The calcium accumulation is seen within hours of a concussion and persists for two to four days after an event. Additionally, cerebral swelling as a result of calcium and sodium influx occurs post concussion and further exposes the patient to additional risk as secondary injury to the brain. See Giza, C. C. and Hovda, D. A. The Neurometabolic Cascade of Concussion. I Athletic Training. 2001, 36(3), 228-235, which describes the series of events following a concussion, including the associated chemical pathways.

Leading developments in these chemical imbalances focus on the calcium influx. According to National Institute of Neurological Disorders and Stroke (NINDS), "Discussion on Traumatic Brain Injury: Hope through Research", Apr. 15, 2011, "[o]ne area of research that shows promise is the study of the role of calcium ion influx into the damaged neuron as a cause of cell death and general brain tissue swelling. Calcium enters nerve cells through damaged channels in the axon's membrane. The excess calcium inside the cell causes the axon to swell and also activates chemicals, called proteases, that break down proteins. One family of proteases, the calpains, are especially damaging to nerve cells because they break down proteins that maintain the structure of the axon. Excess calcium within the cell is also destructive to the cell's mitochondria, structures that produce the cell's energy. Mitochondria soak up excess calcium until they swell and stop functioning. If enough mitochondria are damaged, the nerve cell degenerates. Calcium influx has other damaging effects: it activates destructive enzymes, such as caspases that damage the DNA in the cell and trigger programmed cell death, and it damages sodium channels in the cell membrane, allowing sodium ions to flood the cell as well. Sodium influx exacerbates swelling of the cell body and axon. NINDS researchers have shown, in both cell and animal studies that giving specialized chemicals can reduce cell death caused by calcium ion influx." NIH. www.ninds.nih.gov/disorders/tbi/detail_tbi.htm.

Pain blockers are already known to inhibit the calcium channels, such as neuropathic pain blockers known as N-type voltage-gated calcium channel blockers (N-type VGCC blockers). A recent approach in the treatment of traumatic brain injury is research using N-type VGCC blockers such as SNX-111 (Zirconotide) (Samii et al.) and SNX-185 (Lee et al.; Shahlaie et al.) in studies with rats, which were found to be effective as neuropathic pain blockers and as neuroprotective agents in traumatic brain injury. See, Samii, A.; Badie, H.; Fu, K.; Luther, R. R. and Hovda, D. A. Effects of an N-type calcium channel antagonist (SNX 111; Ziconotide) on calcium-45 accumulation following fluid-percussion injury. I Neurotrauma. 1999, October, 16(10), 879-92; Lee, L. L.; Galo, E.; Lyeth, B. G.; Muizelaar, J. P. and Berman, R. F. Neuroprotection in the rat lateral fluid percussion model of traumatic brain injury by SNX-185, an N-type voltage-gated calcium channel blocker. Exp. Neurol. 2004, November, 190 (1), 70-8; and Shahlaie, K.; Lyeth, B. G.; Gurkoff, G. G.; Muizelaar, J. P. and Berman, R. F. Neuroprotective Effects of Selective N-Type VGCC Blockade on Stretch-Injury-Induced Calcium Dynamics in Cortical Neurons. J. Neurotrauma. 2010, January, 27(1), 175-187.

The research on pain blockers with effects on brain injury recovery has been extended to human applications. For example, SNX-111 was recently found to be biologically active as a therapeutic agent in humans for the treatment of neuropathic pain and for neuroprotection after ischemic brain injury. McGuire, D.; Bowersox, S.; Fellmann, J. D. and Luther, R. R. Sympatholysis After Neuron-Specific, N-Type, Voltage-Sensitive Calcium Channel Blockade: First Demonstration of N-Channel Function in Humans. J. Cardiovascular Pharmacology. 1997, September, 30(3), 400-403.

The prior art studies show a reduction of trauma-induced calcium accumulation in the cerebral cortex and especially the hippocampus tissue. This work using N-type VGCC neuropathic pain blockers is encouraging for treating posttraumatic calcium accumulation using other neuropathic pain blockers that limit the calcium levels of traumatic brain injury.

Gallium compounds are also known effective drugs for reducing calcium levels in hypercalcemia patients and treating neuropathic pain, like N-type VGCC blockers. Gallium compounds have been studied for a variety of neurological aliments (Bernstein, U.S. Pat. No. 8,168,214). Gallium compounds are used to inhibit bone calcium loss (hypercalcemia) in cancer patients. See Warrell, R. P.; Brockman, R. S.; Coonley, C. J.; Isaacs, M. and Staszewski, H. Gallium nitrate inhibits calcium resorption from bone and is effective treatment for cancer-related hypercalcemia. I Clinical Investigation. 1984, 73, 1487-1490; and Todd, P. A. and Fitton, A. Gallium nitrate. A review of its pharmacological properties and therapeutic potential in cancer related hypercalcemia. Drugs. 1991, August, 42(2), 261-73 regarding use of gallium nitrate. Also, Bradley, et al., U.S. Pat. No. 5,196,412, describes compounds of gallium (III), which can be given orally to achieve high serum levels of gallium (III) for the treatment of hypercalcemia of malignancy and related disorders of bone metabolism.

Gallium compounds are known to both rapidly reduce edema in animals and humans. For example Gerber et al., U.S. Pat. No. 5,700,487, discloses a method of treating pulmonary inflammation in mammals, comprising administering an effective amount of a pharmaceutically acceptable gallium compound and wherein said gallium is elected from the group consisting of gallium nitrate, gallium citrate, gallium chloride, gallium carbonate, gallium acetate, gallium tartrate, gallium oxalate, gallium oxide, gallium arsenide and hydrated gallium oxide.

Julian, U.S. Pat. No. 7,354,952, discloses novel pharmaceutical gallium compositions, including gallium complexes having increased oral bioavailability relative to uncomplexed gallium salts. Such compositions are useful in the treatment of conditions and diseases in which inhibition of abnormally increased calcium resorption is desired, including cancer, hypercalcemia, osteoporosis, osteopenia and Paget's disease.

Jiang et al., U.S. Pat. No. 7,119,217, incorporated herein by reference, discloses novel tri(alkylcarboxylato) gallium (III) compounds, exemplified by tripalmitato gallium (III), methods for making them, pharmaceutical compositions containing them, and methods of using the pharmaceutical compositions. These compounds may be useful especially since a DHA is a member of this family of compounds.

Gallium compounds are known treatment in humans for cancer and pain. U.S. Pat. No. 4,704,277 shows that doses of 100-300 mg/sq mm m/day of gallium nitrate over 5-7 days reduce calcium excretion by 70+18%. In the cancer treatments, the gallium appears to inhibit calcium resorption from bone and the exact mechanism is unknown although it could be a reaction with the calcium apatite bone structure binding the calcium into a harder bone structure.

Gallium nitrate is a particular gallium compound. Gallium nitrate is known to treat mammals for pain and anti-bacterial agents. Matkovic et al., U.S. Pat. No. 5,175,006 discloses inflammation pain treatment, and Gerber et al., U.S. Pat. No. 5,700,487, describes pulmonary inflammation treatment in humans and animals. Gallium compounds are also powerful antibacterial and anti-pathogenic agents as taught by Schlesinger et al., U.S. Pat. No. 6,203,822, which further discloses the use of gallium-containing compounds to inhibit intracellular pathogens including pathogens that are members of the genus *Mycobacteria, Legionella, Histoplasma*, and *Leishmania* and to organisms causing chronic pulmonary infection such *P. aeruginosa*. Additionally, gallium nitrate has been shown to be an effective for wound treatment as taught by Rogosnitzky, U.S. Pat. App. Pub. No. 20110104246, as a pharmaceutical composition and method for topical wound treatment by topical treatment with gallium salts, preferably gallium nitrate.

Prior art studies have characterized the chemical imbalances that result from after a traumatic brain injury or concussion. Traumatic brain injury is associated with chemical imbalances at the blood brain barrier and in the brain. There are molecular biomarkers of this chemical imbalance, and these biomarkers are oxidatively modified to carbonyl groups, such that oxidative stress levels indicate the presence of these biomarkers. See Mendes Arent, Andre, Luiz Felipe de Souza, Roger Wals, and Alcir Luiz Dafre, "Perspectives on Molecular Biomarkers of Oxidative Stress and Antioxidant Strategies in Traumatic Brain Injury" BioMed Research International, vol. 2014, Article ID 723060, http://dx.doi.org/10.1155/2014/723060. The calcium influx is still present from the injury, but a further indicator of a concussion is increase in oxidative stress levels by an influx of reactive oxygen species (ROS). The reactive oxygen species (ROS) are highly reactive molecules, which damage cellular components. The reactive oxygen species (ROS) are harmful molecules with free radicals to damage DNA, lipids, and proteins, resulting in cell death. ROS is difficult to measure because the short life span. Thus, indirect measurements of ROS by protein carbonyls and protein nitration can indicate levels of oxidative stress. See Abdul-Muneer, P. M., Heather Schuetz, Fang Wang, Maciej Skotak, Joselyn Jones, Santhi Gorantla, Matthew C. Zimmerman, Namas Chandra, and James Haorah "Induction of Oxidative and Nitrosative damage leads to Cerebrovascular Inflammation in Animal Model of Mild Traumatic Brain Injury Induced by Primary Blast", Free Radical Biol. Med., 2013 July; 60:282-291.

It is an object of the present invention to provide a treatment for traumatic brain injury or concussion.

It is another object of the present invention to provide a treatment for traumatic brain injury or concussion with a gallium compound.

It is still another object of the present invention to provide a treatment for traumatic brain injury with a gallium compound to prevent secondary injury to the brain after the initial injury.

It is still another object of the present invention to provide a treatment for traumatic brain injury to prevent secondary injury to the brain by reducing oxidative stress levels in the brain, after the initial injury.

These and other objects and advantages of the present invention will become apparent from a reading of the attached specification and appended claims.

SUMMARY OF THE INVENTION

A traumatic brain injury is characterized by a chemical imbalance in the brain due to the initial injury, including a cascade of biomarkers of the initial injury. The cascades result in additional chemical processes, which end in a secondary injury to the brain. In particular, after the first hit, the chemical imbalances cause the brain to swell, so that brain receives additional lesions, even after the initial lesion. For treatment of the concussion, stopping these secondary injuries, such as lesions, hematomas, and edemas, is a major concern. Disrupting the cascades can reduce or prevent the secondary injuries for effective treatment of traumatic brain injury. One of the known cascades is the influx of calcium, and pain blockers are known to inhibit calcium channels, during the treatment of pain. Gallium compounds are also known to be similar to the neuropathic pain blockers, and gallium compounds have already been determined to be safe for treatment in humans for pain and even cancer. One of the other known cascades is oxidative stress or mitochondrial oxidative metabolism. Thus, oxidative stress level is a metric of a concussion, showing increases after the initial injury as the chemical imbalances trigger cascades and cascades of other reactions to swell the brain. Even if known to affect calcium levels for pain, the present invention discloses gallium compounds to disrupt the increase in oxidative stress level.

The present invention is a method for treating traumatic brain injury in a mammal by administering a therapeutically effective amount of a pharmaceutically acceptable gallium compound to a blood brain barrier of the mammal within a therapeutically effective time period subsequent to the injury so as to reduce secondary injury in a brain of the mammal. The proper amount of the gallium compound delivered to the brain at a time of increasing oxidative stress after the initial injury disrupts the cascades of chemical imbalances resulting in secondary injuries. The present invention is a treatment for concussions by reducing secondary injuries to the brain.

DETAILED DESCRIPTION OF THE DRAWINGS

Figure 1:
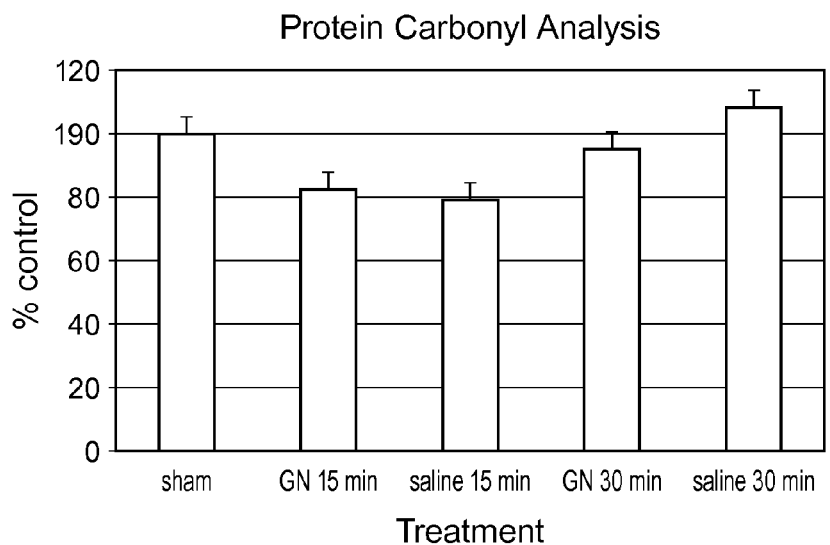
FIG. 1 is a graph illustration of protein carbonyl analysis, showing effects on oxidative stress levels of the present invention.

The method for treating traumatic brain injury in a mammal comprises the step of administering a therapeutically effective amount of a pharmaceutically acceptable gallium compound to a blood brain barrier of the mammal within a therapeutically effective time period subsequent to the injury so as to reduce secondary injury in a brain of the mammal. Secondary injuries include swelling of the brain after the initial injury, secondary lesions, hematomas, and edema. Changes in cerebral perfusion pressure, intracranial pressure, and cerebral blood flow result from the initial injury and secondary injuries. Traumatic brain injuries can range from mild to moderate to severe, although the chemical imbalances are in common.

The gallium compound of the present invention is disclosed. The action of the gallium compound is two-fold since gallium compounds are known to reduce hypercalcemia in cancer patients and also have been shown to reduce edema in animals and humans. Safe and effective amounts of gallium compounds have been approved for treatment in the past. The gallium compound is selected from a group consisting of: gallium nitrate, gallium citrate, gallium chloride, gallium fluoride, gallium phosphate, gallium carbonate, gallium acetate, gallium tartrate, gallium oxalate, gallium formate, gallium oxide, gallium sulfate, gallium arsenide, gallium maltolate, gallium 8-quinolinolate and hydrated gallium oxide, gallium pyridinones, gallium succinate, gallium gluconate, gallium 3-hydroxy-4-pyrone, gallium palmitrate, the tridocosahexaenonic acid salt of gallium, or other tri(alkyl-carboxylato) gallium (III) compounds, gallium prophyrins, gallium transferrins, gallium pyridoxal isonicotinoyl hydrazine, and combinations thereof. In particular, gallium nitrate and a docosahexaenonic acid salt of gallium, have been disclosed for hypercalcemia and/or related to the docosahexaenoic acid (DHA), the current treatment for concussion. The docosahexaenonic acid salt of gallium with one to three of the gallium ligands being from docosahexaenonic acid is also related to DHA. The docosahexaenonic acid salt of gallium is a fatty acid triglyceride salt with known combination to one to three DHA molecules, also being fats.

The step of administering includes delivery to the blood brain barrier in known vectors, including orally, by injection, intravenously, subcutaneously, transdermally, intramuscularly, and by inhalation. Injection includes intraperitoneal injection. Transdermal delivery includes patches, passive transdermal single-layer technology, multi-layer drug-in-adhesive technology, and microneedle systems. Inhalation includes delivery by nasal spray or oral spray. In some embodiments, orally, transdermally, and nasal inhalation are supplied in a first aid kit. Delivery of the gallium compound close to the time of injury can allow time for reaching the blood brain barrier, when the rate of oxidative stress is still increasing. Delivery of the gallium compound to the head of the individual can also be part of the embodiment of the present invention. Attaching a transdermal patch physically close to the brain shortens travel distance of the gallium compound, which can be absorbed through the skin and tissue. At sporting events and athletic practices, the vector can be present for administering the gallium compound, right after the initial injury occurs.

The therapeutically effective amount of a pharmaceutically acceptable gallium compound reduces oxidative stress in the brain of the individual without undue side effects. Pharmaceutically acceptable without undue side effects can be established for reducing oxidative stress levels in the brain of the present invention, just as in prior art treatments for human for pain and cancer. The practice of the present invention will employ, unless otherwise indicated, conventional techniques of drug formulation, which are within the skill of the art. Such techniques are fully explained in the literature. See, for example, REMINGTON: THE SCIENCE AND PRACTICE OF PHARMACY (2000), cited supra, as well as Goodman & Gilman's THE PHARMACOLOGICAL BASIS OF THERAPEUTICS, 9th Ed. (New York: McGraw-Hill, 1996) and Ansel et al., PHARMACEUTICAL DOSAGE FORMS AND DRUG DELIVERY SYSTEMS, 6th Ed. (Media, Pa.: Williams & Wilkins, 1995). Any suitable pharmaceutical formulations that comprise pharmaceutically acceptable gallium compositions may be utilized in the practice of the invention. The level of predictability in the art establishes amounts can be approved for treatment. The treatment for concussion would similarly remain in the effective and healthy ranges for treatment of other conditions.

In embodiments of the present invention, the effective amount ranges from 2-50 mg/kg, preferably 2-20 mg/kg, and the effective time period for delivery to the blood brain barrier ranges from 15 minutes to 60 minutes, preferably 30 minutes. The effective time period ranges from 15 minute to 24 hours, as long as the rate of increasing oxidative stress continues to increase. Range for effective amount is based on known ranges for mammals in other treatments, pharmaceutically confirmed ranges, and test results for the present invention, showing efficacy within the claimed range. Range for effective time period is based on known ranges for increases rates of oxidative stress after initial injury, and test results for the present invention, showing efficacy within the claimed range. Test results support these embodiments of the present invention.

EXAMPLE

Twenty C57BL/6NHsd mice were used for a study. Mice were set into five groups: sham, 15 minutes saline, 15 minutes gallium, 30 minutes gallium, and 30 minutes saline. A moderate controlled cortical contusion was given to all animals except the four animals in the sham group. The 15 minutes gallium group was injected with 10 mg/kg gallium nitrate at 15 minutes post injury. The 15 minutes saline group was injected with saline at 15 minutes post injury. The 30 minutes gallium group was injected with 10 mg/kg gallium nitrate at 30 minutes post injury. The 30 minutes saline group was injected with saline at 30 minutes post injury. A sample size of 4 was used for each group except gallium nitrate treated samples at 15 minutes post injury (n=3), gallium nitrate treated samples at 30 minutes post injury (n=5), and saline treated animals at 30 minutes (n=3).

A gallium compound was delivered by injection, in particular, intraperitoneal injection. One animal was dropped from the study because the animal twisted during injection of gallium nitrate (10 mg/kg) 15 minutes post injury and did not survive. Due to this unequal pairing, statistics (Student's t-test) were performed using unpaired analysis. P values <0.05 were deemed significant. Western blots (slot blots) were run for all samples and immunoblotting was performed with the following antibodies 2,4-DNP (protein carbonyls) and anti-3-nitrotyrosine (protein nitration). All blots were run twice for reproducibility. All samples were compared to sham (craniotomy only, but no injury), which has been used as a baseline (control).

Figure 2:
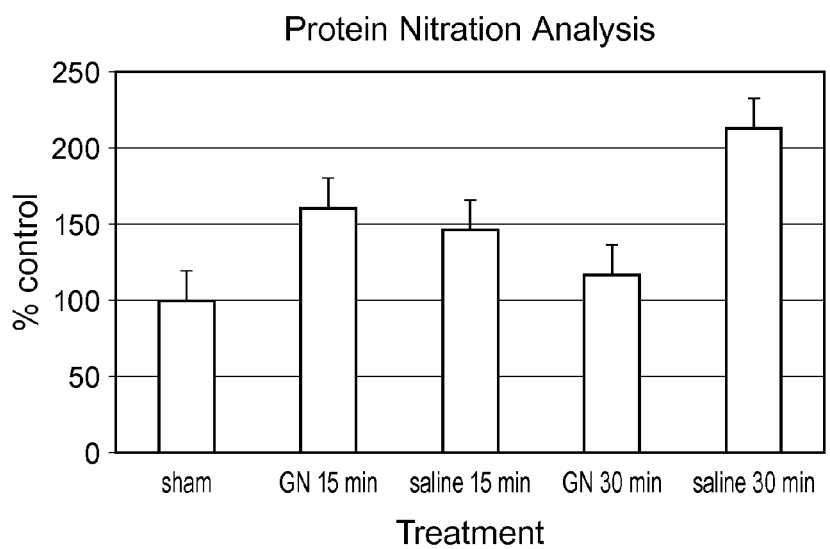
FIG. 2 is a graph illustration of protein nitration by indexing levels of 3-nitrotyrosine, showing effects on oxidative stress levels of the present invention.

The two parameters for oxidative stress were run on whole brain homogenate using immunochemical detection. Protein carbonyls, a marker of overall oxidative stress, were evaluated, as shown in FIG. 1. Protein nitration by indexing levels of 3-nitrotyrosine (3-NT) was determined, as shown in FIG. 2.

TABLE 1

Protein Carbonyl Analysis

| Treatment | Difference compared to control (sham) |
|---|---|
| Sham | — |
| Gallium nitrate at 15 minutes post injury | 17.5% reduction |
| Saline at 15 minutes post injury | 20.5% reduction |
| Gallium nitrate at 30 minutes post injury | 6.6% reduction |
| Saline at 30 minutes post injury | 8.3% increase |

The sham is the control because the animals did not receive a concussion. The two saline groups should promote oxidative stress, which can be observed at 30 minutes but not 15 minutes. Gallium nitrate treatment at both time points showed a reduction in oxidative stress.

TABLE 2

Protein Nitration Analysis

| Treatment | Difference compared to control (sham) |
|---|---|
| Sham | — |
| Gallium nitrate at 15 minutes post injury | 61.3% increase |
| Saline at 15 minutes post injury | 47.3% increase |
| Gallium nitrate at 30 minutes post injury | 18.1% increase |
| Saline at 30 minutes post injury | 114% increase |

Protein nitration is determined by indexing levels of 3-nitrotyrosine (3-NT). The sham is the control because the animals did not receive a concussion. The two saline groups showed increases in 3-nitrotyrosine (3-NT) levels over time, including a 2.4 fold increase over 15 minutes. Gallium nitrate treatment groups showed an increase in the levels of 3-NT at 15 minutes, but showed a significant reduction in the levels of 3-NT at 30 minutes. The results demonstrate a reduction in protein nitration at 30 minutes. The difference between saline groups and the gallium groups at 30 minutes was statistically significant.

Oxidative stress was more prominent at 30 minutes in the saline groups, which is indicative of oxidative stress increasing over time as expected. From protein carbonylation and protein nitration, there is a demonstrable effect of the gallium compound. The timing of the dosing also appears to matter, since results at 15 minutes differed from results at 30 minutes. For the protein carbonylation, the treatment was reducing overall oxidative stress, but the earlier 15 minute group reduced more than the 30 minute group. For the protein nitration, the treatment shows better results at the 30 minute group with more reduction at the later time. The test results show an overall benefit for administering a gallium compound to reduce oxidative stress. There is a reduction after the initial injury, and administering the gallium compound can be shown to have benefits with second and even third doses, after a first dose. The trend still shows effectiveness at reducing the increases in oxidative stress. As long as the oxidative stress is increasing, the present invention can be used to reduce the increases.

Additionally, the test results show a "sweet spot" between 15 minutes and 30 minutes for reducing the oxidative stress. The reduction by a protein carbonylation is best earlier than reduction by protein nitration, which is best later. Optimizing the effective time period for the first dose would not require undue experimentation based on the current results.

A third possible metric is lipid peroxidation analysis by assessing 4-hydroxynoneal binding. Lipid peroxidation is another indicator of oxidative stress levels, although different chemical pathways are involved, compared to both protein carbonylation and protein nitration.

The present invention establishes a treatment for traumatic brain injury or concussion. An effective amount of a gallium compound administered to the blood brain barrier, after the initial injury, reduces oxidative stress levels in the brain. Oxidative stress levels increase during the cascade of reactions caused by chemical imbalances in the brain from the initial injury. The cascades result in secondary injury to the brain, hours and days, after the initial injury. Capping the increases on the oxidative stress by the effective amount of gallium compounds delivered to the blood brain barrier can slow the reactions that cause the swelling and secondary injuries. Additionally, there is an effective time period for the administering the first dose of the gallium compound, after the injury. Some reactions to reduce oxidative stress happen earlier, not later. The second and third and any subsequent doses of gallium compound are still supported by the overall trend of reduction in increases of rates of oxidative stress over time. There can be a different effective amount at a later time or at a time after the first dose. The present invention includes the embodiments of subsequent steps of administering later doses of the gallium compound.

All references referred to herein are incorporated herein by reference. While the apparatus, systems and methods of this invention have been described in terms of preferred or illustrative embodiments, it will be apparent to those of skill in the art that variations may be applied to the process and system described herein without departing from the concept and scope of the invention. All such similar substitutes and modifications apparent to those skilled in the art are deemed to be within the scope and concept of the invention. Those skilled in the art will recognize that the method and apparatus of the present invention has many applications, and that the present invention is not limited to the representative examples disclosed herein. Moreover, the scope of the present invention covers conventionally known variations and modifications to the system components described herein, as would be known by those skilled in the art.

The foregoing disclosure and description of the invention is illustrative and explanatory thereof. Various changes in the details of the illustrated construction can be made without departing from the true spirit of the invention.

I claim:

1. A method of treating traumatic brain injury in a mammalian individual, said method comprising the steps of:
   administering a therapeutically effective amount of a pharmaceutically acceptable gallium compound to a blood brain barrier of the individual within a therapeutically effective time period subsequent to the injury so as to reduce secondary injury in a brain of the individual.

2. The method of treating traumatic brain injury, according to claim 1, wherein the effective amount reduces oxidative stress in said brain.

3. The method of treating traumatic brain injury, according to claim 1, wherein the effective amount ranges from 2-50 mg/kg.

4. The method of treating traumatic brain injury, according to claim 1, wherein the effective amount ranges from 2-20 mg/kg.

5. The method of treating traumatic brain injury, according to claim 1, wherein the effective time period ranges from 15 minutes to 30 minutes.

6. The method of treating traumatic brain injury, according to claim 1, wherein the effective time period is 30 minutes.

7. The method of treating traumatic brain injury, according to claim 1, wherein the effective time period ranges from 15 minutes to 24 hours.

8. The method of treating traumatic brain injury, according to claim 1, wherein the effective time period is as along as the rate oxidative stress increases, after said initial injury.

9. The method of treating traumatic brain injury, according to claim 1, wherein said gallium compound is selected from a group consisting of: gallium nitrate, gallium citrate, gallium chloride, gallium fluoride, gallium phosphate, gallium carbonate, gallium acetate, gallium tartrate, gallium oxalate, gallium formate, gallium oxide, gallium sulfate, gallium arsenide, gallium maltolate, gallium 8-quinolinolate and hydrated gallium oxide, gallium pyridinones, gallium succinate, gallium gluconate, gallium 3-hydroxy-4-pyrone, gallium palmitrate, the tridocosahexaenonic acid salt of gallium, or other tri(alkylcarboxylato) gallium (III) compounds, gallium prophyrins, gallium transferrins, gallium pyridoxal isonicotinoyl hydrazine, and combinations thereof.

10. The method of treating traumatic brain injury, according to claim 1, wherein said gallium compound is comprised of gallium nitrate.

11. The method of treating traumatic brain injury, according to claim 1, wherein said gallium compound is comprised of a docosahexaenonic acid salt of gallium with one to three of the gallium ligands being from docosahexaenonic acid.

12. The method of treating traumatic brain injury, according to claim 1, wherein said gallium compound is administered orally.

13. The method of treating traumatic brain injury, according to claim 1, wherein said gallium compound is administered by injection.

14. The method of treating traumatic brain injury, according to claim 1, wherein said gallium compound is administered by intraperitoneal injection.

15. The method of treating traumatic brain injury, according to claim 1, wherein said gallium compound is administered by transdermal patch.

16. The method of treating traumatic brain injury, according to claim 1, wherein said gallium compound is administered by nasal spray.

17. The method of treating traumatic brain injury, according to claim 1, further comprising the step of:
   administering another therapeutically effective amount of said pharmaceutically acceptable gallium compound to said blood brain barrier of the individual after said therapeutically effective time period subsequent to the injury so as to continue reducing secondary injury at a brain of the individual.

18. The method of treating traumatic brain injury, according to claim 17, further comprising the step of:
   administering still another therapeutically effective amount of said pharmaceutically acceptable gallium compound to said blood brain barrier of the individual after administering said another therapeutically effective amount so as to continue reducing secondary injury at a brain of the individual.

* * * * *